United States Patent [19]

Chi et al.

[11] Patent Number: 5,156,998
[45] Date of Patent: Oct. 20, 1992

[54] BONDING OF INTEGRATED CIRCUIT CHIP TO CARRIER USING GOLD/TIN EUTECTIC ALLOY AND REFRACTORY METAL BARRIER LAYER TO BLOCK MIGRATION OF TIN THROUGH VIA HOLES

[75] Inventors: Tom Y. Chi, San Gabriel; Brook D. Raymond, Hermosa Beach, both of Calif.

[73] Assignee: Hughes Aircraft Company, Los Angeles, Calif.

[21] Appl. No.: 767,949

[22] Filed: Sep. 30, 1991

[51] Int. Cl.⁵ ............................................ H01L 21/58
[52] U.S. Cl. ...................................... 437/209; 437/902
[58] Field of Search ............... 437/209, 902, 939, 946; 148/DIG. 56; 428/620, 627, 646, 647

[56] References Cited

U.S. PATENT DOCUMENTS

| | | | |
|---|---|---|---|
| 4,603,455 | 8/1986 | Woest et al. | 29/25.42 |
| 4,702,967 | 10/1987 | Black et al. | 428/627 |
| 4,927,505 | 5/1990 | Sharma et al. | 428/620 |
| 5,027,189 | 6/1991 | Shannon et al. | 357/68 |
| 5,063,177 | 11/1991 | Geller et al. | 437/209 |

Primary Examiner—Olik Chaudhuri
Assistant Examiner—David E. Graybill
Attorney, Agent, or Firm—Jeannette M. Walder; Terje Gudmestad; W. K. Denson-Low

[57] ABSTRACT

A gallium arsenide monolithic microwave integrated circuit (MMIC) chip (12) has microelectronic devices (16,18) formed on a frontside surface (12a), and via holes (12c,12d) formed through the chip (12) from the frontside surface (12a) to the backside surface (12b). The backside surface (12b) of the chip (12) is bonded to a molybdenum carrier (14) by an eutectic gold/tin alloy (20). A barrier layer (22) including a refractory metal nitride material (22a) is sputtered onto the backside surface (12b) and into the via holes (12c,12d) of the chip (12) prior to bonding. The barrier layer (22) blocks migration of tin from the eutectic gold/tin alloy (20) through the via holes 12c,-12d) to the frontside surface (12a) of the chip (12) during the bonding operation, thereby preventing migrated tin from adversely affecting the microelectronic devices (16,18).

10 Claims, 2 Drawing Sheets

BONDING OF INTEGRATED CIRCUIT CHIP TO CARRIER USING GOLD/TIN EUTECTIC ALLOY AND REFRACTORY METAL BARRIER LAYER TO BLOCK MIGRATION OF TIN THROUGH VIA HOLES

BACKGROUND OF THE INVENTION

1. Field of the Invention

The present invention generally relates to the fabrication of microelectronic integrated circuits, and more specifically to the bonding of a monolithic microwave integrated circuit (MMIC) chip to a carrier using an eutectic gold/tin (Au/Sn) alloy.

2. Description of the Related Art

The eutectic chip bonding process is widely used in the fabrication of radar and other microwave systems including gallium arsenide (GaAs) microelectronic integrated circuits, especially MMIC chips. These chips have microelectronic devices formed on a frontside surface, and via holes formed therethrough from the frontside surface to a backside surface. The via holes are necessary for grounding, and reducing the source inductance and resistance of field-effect transistor (FET) devices formed on the frontside surface of the chip.

The backside surfaces of the chips are bonded to molybdenum carriers using an eutectic alloy, the most widely used of which is gold/tin. This alloy enables fusion of GaAs MMIC chips to carriers at an eutectic temperature on the order of 280° C., which is much lower than the individual melting points of the constituent elements of the alloy, such that bonding can be performed at a temperature low enough to preclude damage to the chips. In addition, the eutectic gold/tin alloy has very high thermal conductivity, which is essential for providing heat dissipation from high-power GaAs MMIC chips to carriers. The basic eutectic bonding process using gold/tin alloy is described in an article entitled "Void-free Au-Sn Eutectic Bonding of GaAs Dice and its Characteristic Using Scanning Acoustic Microscopy", by G. Matijasevic et al, in Journal of Electronic Materials, Vol. 18, No. 2, part 2, March 1989, pp. 327-337.

A problem which has prevailed in eutectic gold/tin alloy bonding is migration of tin through the via holes to the frontside surfaces of the chips during the bonding operation. Tin is highly mobile, and migrates quickly to the surface of the alloy, and upwardly through the via holes, upon heating of the alloy above the eutectic temperature. Contamination of microelectronic devices on the frontside surfaces of MMIC chips by tin migration results in severe degradation of the electronic performance of the devices.

Attempts to prevent tin migration through via holes have included forming metal films or layers on the backside surfaces of chips prior to bonding. Nickel (Ni) and platinum (Pt) films have been used. The most common process includes sputtering a layer including sublayers of Ti/Pt/Au having thicknesses of 500/1,000/1,500 angstroms respectively onto the backside surfaces of the chips, followed by a plated layer including sublayers of Au/Ni/Au having thicknesses of 1.5/1.0/1.0 micrometers respectively.

Although metal films retard tin migration through the via holes, they do not block it completely, and are only effective in reducing the tin migration and resulting device contamination. In addition, the combined thickness of the sputtered and plated layers is approximately 4 micrometers. This is much too thick for chip separation using the preferred "scribe-and-break" process, which requires that the backside metal be less than approximately one micrometer thick. Chip separation must be performed using the "saw-cut" process, which is much more time consuming, expensive, and prone to breakage than the scribe-and-break process.

Refractory metal nitride layers have been used per se in the fabrication of FETs on silicon substrates. The nitride layers are formed between the aluminum contact metallizations and the sources, drains and gates of the FETs to prevent contamination thereof by aluminum from the contacts. This process is described in an article entitled "TiN Formed by Evaporation as a Diffusion Barrier Between Al and Si", by G. Ting, in Journal of Vacuum Science Technology, 21(1), May/June 1982, pp. 14-18.

Similar refractory metal nitride layers have been employed to prevent diffusion between gold contacts and GaAs substrates, such as described in an article entitled "Use of a TiN Barrier to Improve GaAs Ohmic Contact Reliability", by R. Remba et al, in IEEE Electron Device Letters, Vol. EDL-6, No. 8, Aug. 1985, pp. 437-438.

However, the problem of tin migration from the backside surfaces of substrates through via holes to the frontside surfaces during eutectic bonding of GaAs MMICs is substantially different from the problem of diffusion between contact metallizations, which are formed on the frontside surfaces, and the substrate material itself. The only materials which have been previously applied for retarding tin migration in GaAs MMICs have been nickel and platinum as described above.

SUMMARY OF THE INVENTION

The present invention provides an improved eutectic chip bonding method, and an integrated circuit chip assembly fabricated using the method.

In accordance with the invention, a gallium arsenide monolithic microwave integrated circuit (MMIC) chip has microelectronic devices formed on a frontside surface, and via holes formed through the chip from the frontside surface to a backside surface. The backside surface of the chip is bonded to a molybdenum carrier by an eutectic gold/tin alloy. A barrier layer including a refractory metal nitride material is sputtered onto the backside surface and into the via holes of the chip prior to bonding.

The barrier layer blocks migration of tin from the eutectic gold-tin alloy through the via holes to the frontside surface of the chip during the bonding operation, thereby preventing migrated tin from adversely affecting the microelectronic devices. This substantially increases the reliability and operating lifetime of the devices.

The barrier layer includes a refractory metal nitride sublayer layer, which may be titanium nitride, tantalum nitride or titanium tungsten nitride formed on the backside surface of the chip, and a gold sublayer formed on the nitride sublayer to adhere the nitride sublayer to the eutectic gold-tin alloy. A titanium sublayer may optionally be provided between the nitride sublayer and the backside surface of the chip to enhance adhesion of the nitride sublayer to the GaAs chip.

The thickness of the barrier layer is less than the one micrometer maximum thickness requirement for the scribe-and-break chip separation process. This enables the yield and throughput to be substantially increased over the prior art method which uses thick nickel and platinum backside layers since the scribe-and-break chip separation process may be advantageously used rather than the saw-cut process as required by the prior art.

These and other features and advantages of the present invention will be apparent to those skilled in the art from the following detailed description, taken together with the accompanying drawings, in which like reference numerals refer to like parts.

DETAILED DESCRIPTION OF THE INVENTION

Figure 1:
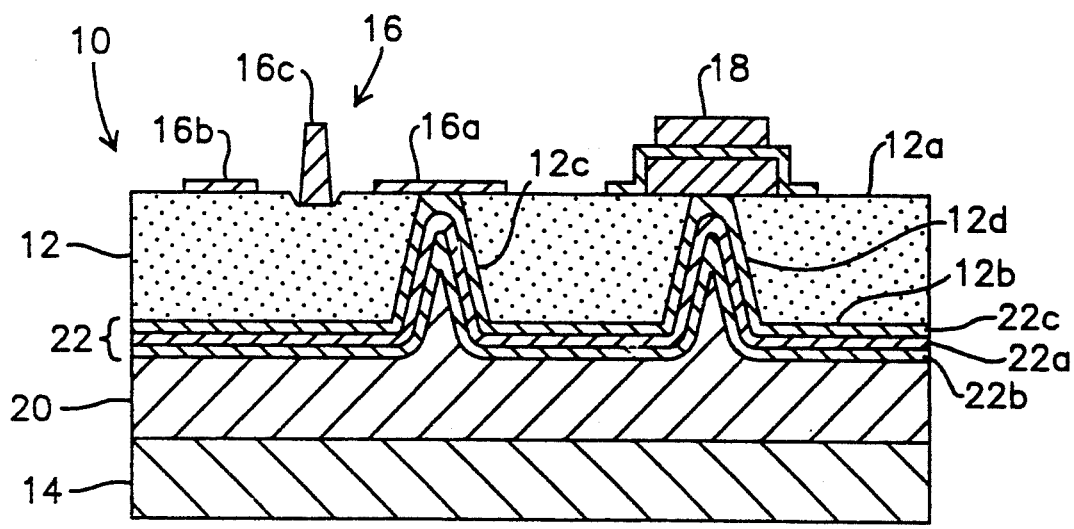
FIG. 1 is a simplified, partial sectional view of an integrated circuit chip assembly fabricated using the method of the present invention.

Referring to FIG. 1, an integrated circuit chip assembly fabricated by a process or method embodying the present invention is generally designated as 10, and includes a GaAs MMIC integrated circuit chip 12. The chip 12 has a frontside surface 12a, a backside surface 12b, and via holes 12c and 12d formed therethrough between the surfaces 12a and 12b. Microelectronic devices are fabricated on the frontside surface 12a, whereas the backside surface 12b is bonded to a molybdenum chip carrier 14.

The microelectronic devices may be of any applicable type, including FETs, resistors, capacitors, etc. interconnected by microstrip waveguides. Illustrated by way of example are an FET 16 and a capacitor 18. The FET 16 includes source, drain, ohmic contact and gate metallizations 16a, 16b and 16c respectively. The source metallization 16a is connected to the chip carrier 14 through the via hole 12c. The capacitor 18 has one plate (not designated) connected to the carrier 14 through the via hole 12d.

The chip 12 is bonded to the carrier 14 by means of an eutectic alloy layer or "preform" 20, including 80% gold and 20% tin. The preform 20 is provided in the form of a sheet or film approximately 12.7 micrometers thick which is sandwiched between the chip 12 and carrier 14, and the assembly 10 is heated to a temperature of approximately 280° C. (slightly above the eutectic temperature of the alloy) such that the preform 20 fuses and bonds the chip 12 to the carrier 14.

During the bonding step, if the bonding was performed without the improvement of the invention, alloy from the preform 20 would rise up into and completely fill the via holes 12c and 12d, providing direct electrical and thermal contact with the metallization 16a and capacitor 18 respectively. The tin at the surface of the alloy in the via holes 12c and 12d would contaminate the frontside surface 12a of the chip 12 and the devices formed thereon.

In order to prevent this undesirable effect, the present assembly 10 further includes a barrier layer 22 including a nitride sublayer 22a of a refractory metal nitride material. The sublayer 22a is approximately 500–1,500 angstroms thick, with the preferred thickness being 1,000 angstroms, and formed of titanium nitride (TiN), tantalum nitride (TaN) or titanium tungsten nitride (TiWN).

The barrier layer 22 further includes a gold sublayer 22b to provide adhesion between the nitride sublayer 22a and the preform 14. The gold sublayer 22b is approximately 5,000–10,000 angstroms thick, with the preferred thickness being 6,000 angstroms, although the sublayer 22b may be made thicker if desired.

Although the nitride sublayer 22a is capable of adhering directly to backside surface 12b of the GaAs chip 12, a titanium sublayer 22c may optionally be provided to enhance the adhesion between the nitride sublayer 22a and chip 12. The titanium sublayer 22c is approximately 200–1,000 angstroms thick, with the preferred thickness being 500 angstroms. Although titanium is the preferred material for the sublayer 22c, it will be noted that other materials which enhance adhesion between the GaAs chip 12 and the nitride sublayer 22a, such as chromium (Cr), may be substituted.

The combined thicknesses of the sublayers 22a, 22b and 22c of the barrier layer 22 is less than one micron, enabling the assembly 10 to be processed using the preferred scribe-and-break chip separation method. In the described embodiment of the assembly 10, the total thickness of the barrier layer 22 is $500 + 1,000 + 6,000$ angstroms $= 7,500$ angstroms.

The barrier layer 22 is sputtered onto the backside surface 12b of the chip 12, and intrudes into the via holes 12c and 12d to make electrical and thermal contact with the metallization 16a and capacitor 18 respectively. The barrier layer 22 coats the walls of the via holes 12c and 12d and the portions of the lower surfaces of the metallization 16a and capacitor 18 which overly the via holes 12c and 12d respectively as illustrated. It is necessary that the barrier layer 22 block the via holes 12c and 12d so that alloy from the preform 20 is prevented from flowing upwardly through the via holes to the frontside surface 12a when the alloy is in the fluid state during the bonding operation.

In accordance with the invention, the refractory metal nitride 22a is resistant to migration of tin from the alloy of the preform 20, and positively blocks upward migration of tin through the via holes 12c and 12d. The elimination of tin migration prevents the microelectronic devices on the frontside surface 12a of the chip 12 from being contaminated by tin, thereby enhancing the reliability and operating lifetime of the chip 12. The barrier layer 22 is formed of metals having high electrical and thermal conductivity, thereby providing an effective path from the chip 12 to the carrier 14 through the preform 20 for grounding and heat dissipation.

Figure 2A:
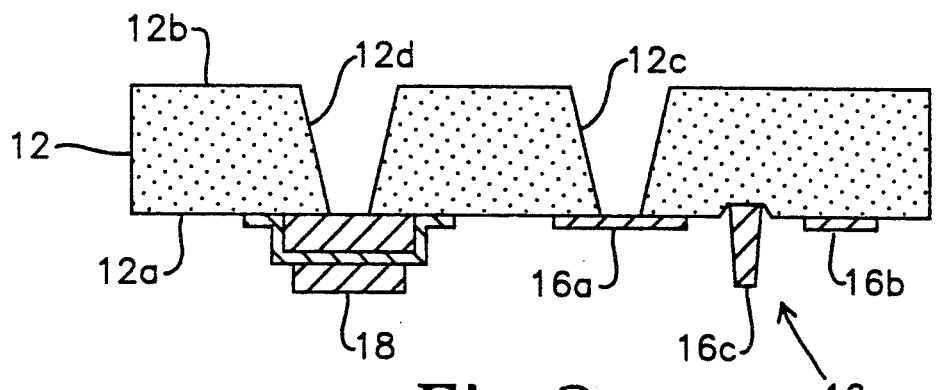
FIGS. 2a to 2e are simplified, partial sectional views illustrating the present method.

The process or method of fabricating the assembly 10 is illustrated in FIGS. 2a to 2e. FIG. 2a shows the chip 12 as being inverted, with the backside surface 12b facing upward. During the various steps of the method, it will be understood that suitable means are provided for supporting the chip 12 and carrier 14, although not shown in the drawing. Further, although the backside surface 12b of the chip 12 is described as being bonded to the chip carrier 14, it will be understood that the preform 20 and barrier layer 22 are interposed between the backside surface 12b and carrier 14.

Figure 2B:
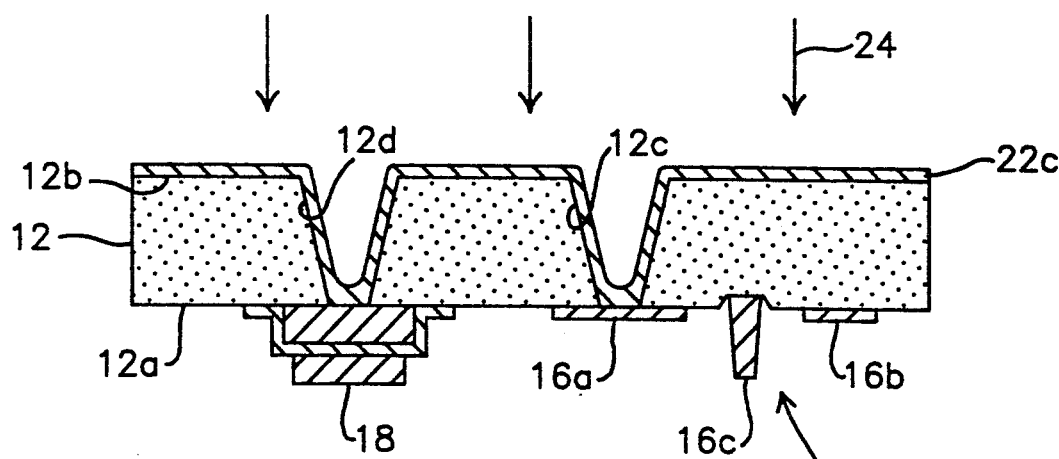

In FIG. 2b, the optional titanium sublayer 22c is sputtered onto the backside surface 12b of the chip 12 using a conventional apparatus (not shown) as symbolically indicated by arrows 24.

Figure 2C:
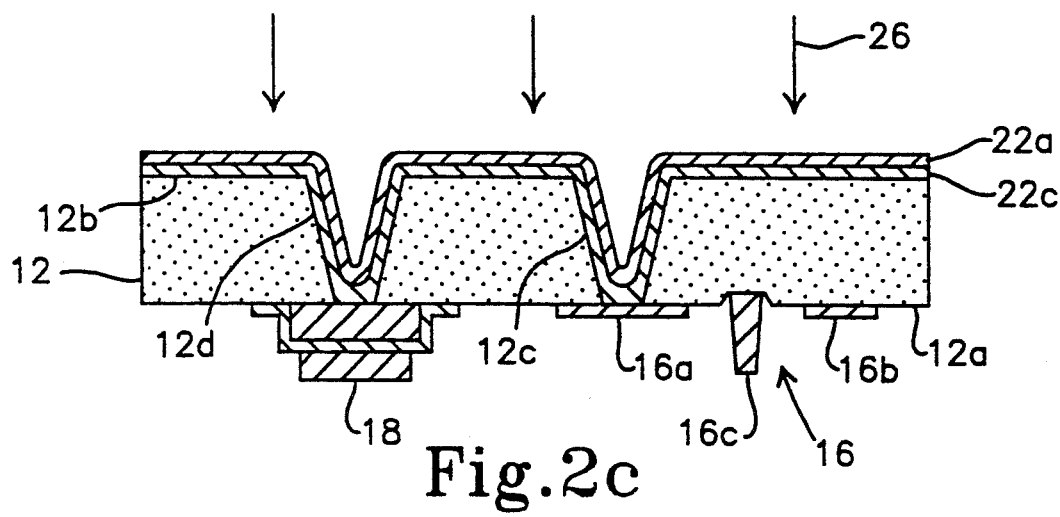

FIG. 2c illustrates the step of sputtering the nitride sublayer 22a onto the backside surface 12b (over the titanium sublayer 22c where provided) as indicated by arrows 26. The nitride sublayer 22a is formed by sputtering a refractory metal target (not shown) with a mixture of argon and nitrogen gas, where the proportion of nitrogen is approximately 1-10% by volume. The nitrogen in the gas mixture reacts with the refractory metal to form the metal nitride, which sputters from the target onto the backside surface 12a of the chip 12.

Figure 2D:
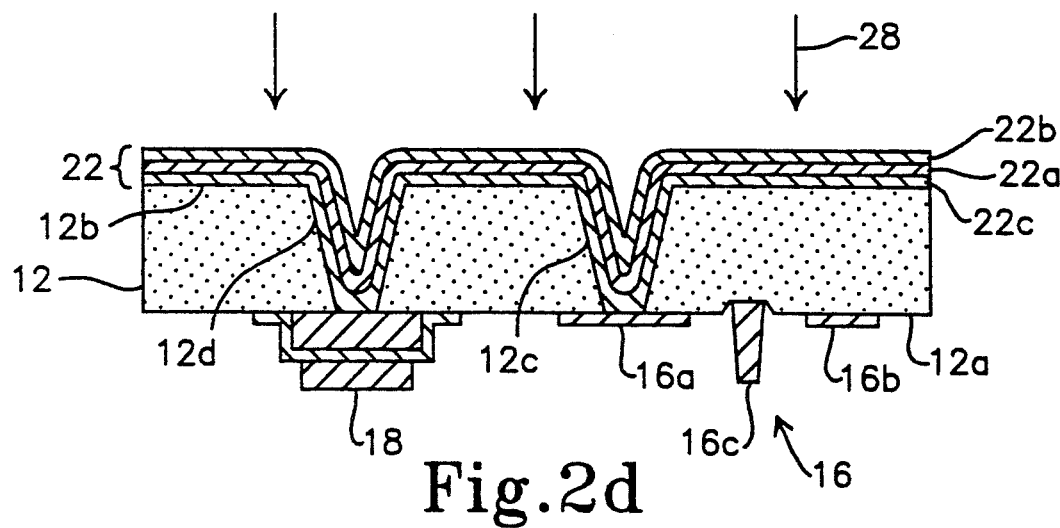

FIG. 2d illustrates the step of sputtering the gold sublayer 22b onto the nitride sublayer 22a as indicated by arrows 28 to form the complete barrier layer 22 on the backside surface 12a of the chip 12.

Figure 2E:
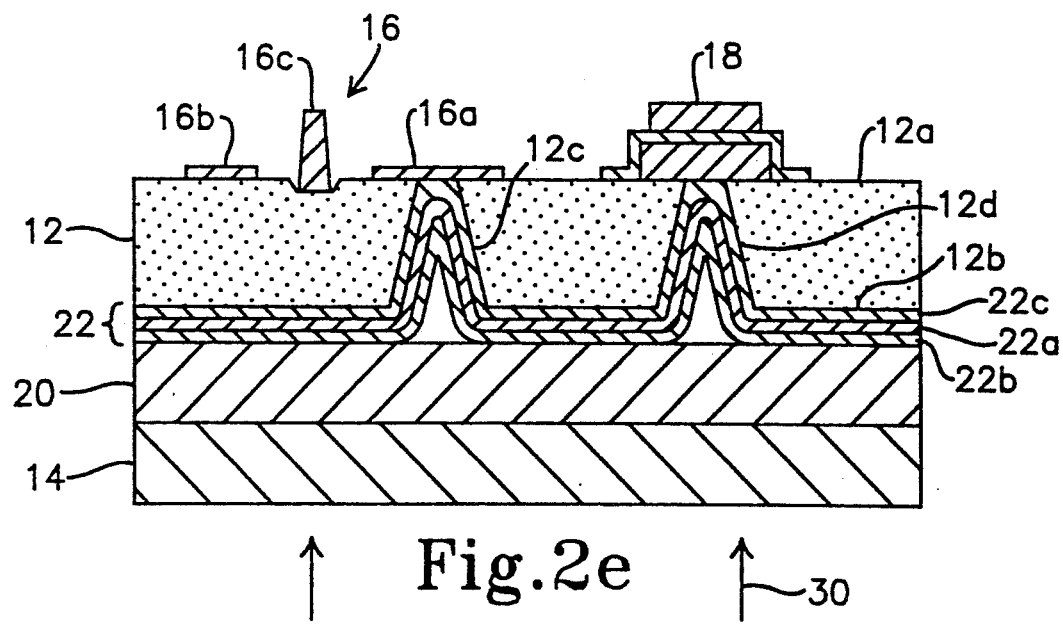

As illustrated in FIG. 2e, the chip 12 with the barrier layer 22 formed thereon is inverted and positioned on the carrier 14, with the preform 20 sandwiched therebetween. Heat is applied as indicated by arrows 30 such that the temperature of the preform 20 is raised above the eutectic temperature of the gold-tin alloy (approximately 280° C.) for 30-40 seconds, and the preform 20 fuses and thereby bonds the chip 12 to the carrier 14. Part of the material of the preform 20 flows upwardly to fill any cavities remaining in the via holes 12c and 12d. The complete assembly 10 illustrated in FIG. 1 is produced after the preform 20 is allowed to cool and solidify.

EXAMPLE

A manual chip bonding process was used to evaluate the effectiveness of the refractory metal nitride barrier layer in preventing migration of tin through the via holes of GaAs MMIC chips. Various combinations of metals were formed on the backside surfaces of identical chips. The chips were bonded to a molybdenum chip carrier using a 12.7 micrometer thick gold-tin alloy preform at 280° C.

Samples 1 and 2 were fabricated using nickel and platinum as the tin migration retarding materials as described above with reference to the prior art. Samples 3 to 6 were fabricated using the method of the present invention. The thicknesses of the various layers were the same as those described above.

Visual inspection was used to determine the time required for tin to migrate to the frontside surfaces of the chips through the via holes. Gold metallization pads which were formed over the via holes were initially yellow in color. Migration of tin, which is white, caused the metallization pads to become contaminated, and the color thereof as observed at the frontside surface of the chip to turn from yellow to white.

| Sample | Migration time |
| --- | --- |
| 1. Plated Au/Ni/Au over sputtered Ti/Au (prior art) | 60-75 seconds |
| 2. Plated Au/Ni/Au over sputtered Ti/Pt/Au (prior art) | 60-75 seconds |
| 3. Sputtered Ti/TaN/Au (gas mixture 1% $N_2$ in Ar) | >300 seconds |
| 4. Sputtered Ti/TiWN/AU (gas mixture 2% $N_2$ in Ar) | >300 seconds |
| 5. Sputtered Ti/TiWN/Au) (gas mixture 6% $N_2$ in Ar) | >300 seconds |
| 6. Sputtered Ti/TaN/Ti/TaN/Au (gas mixture 1% $N_2$ in Ar) | >300 seconds |

For the samples 3 to 6, the bonding process was discontinued after 300 seconds. An eutectic chip bonding process typically requires 30 to 40 seconds for completion. No migration of tin was observed using the method of the present invention after approximately ten times the normal process time had elapsed.

While several illustrative embodiments of the invention have been shown and described, numerous variations and alternate embodiments will occur to those skilled in the art, without departing from the spirit and scope of the invention. Accordingly, it is intended that the present invention not be limited solely to the specifically described illustrative embodiments. Various modifications are contemplated and can be made without departing from the spirit and scope of the invention as defined by the appended claims.

We claim:

1. A method of bonding a backside surface of an integrated circuit chip having a microelectronic device fabricated on a frontside surface thereof, and a via hole formed therethrough between the frontside and backside surfaces thereof, to a carrier, comprising the steps of:
    (a) forming a barrier layer including a refractory metal nitride material on the backside surface and inside the via hole of the chip such that the via hole is blocked by the barrier layer;
    (b) positioning the chip on the carrier with a bonding layer of an eutectic alloy material including tin sandwiched between the backside surface of the chip and the carrier;
    (c) heating the carrier, chip and bonding layer to a temperature above the eutectic temperature of said alloy material to bond the backside surface of the chip to the carrier, said nitride material of the barrier layer blocking migration of tin from said alloy material of the bonding layer through the via hole to the frontside surface of the chip.

2. A method as in claim 1, in which step (a) comprises forming the barrier layer by sputtering.

3. A method as in claim in which step (a) comprises forming the barrier layer such that the thickness of the refractory metal nitride material is approximately 500-1500 angstroms.

4. A method as in claim 1, in which step (a) comprises forming the barrier layer to a thickness selected such that the combined thickness of the barrier layer and bonding layer is less than approximately one micrometer.

5. A method as in claim 1, in which step (a) comprises forming the barrier layer with said nitride material selected from the group consisting of titanium nitride, tantalum nitride and titanium tungsten nitride.

6. A method as in claim 1, in which said alloy material further comprises gold, and after step (a), further comprising the substep of:
    (d) forming a gold sublayer on the nitride sublayer.

7. A method as in claim 6, in which step (a) comprises forming the nitride sublayer with said nitride material selected from the group consisting of titanium nitride, tantalum nitride and titanium tungsten nitride.

8. A method as in claim 6, in which:
    step (a) comprises forming the nitride sublayer to a thickness of approximately 500-1,500 angstroms; and
    step (d) comprises forming the gold sublayer to a thickness of approximately 5,000-10,000 angstroms.

9. A method as in claim 1, in which the chip comprises gallium arsenide, and prior to step (a), further comprising the substep of:
    (d) forming a titanium sublayer on the backside surface of the chip and inside the via hole of the chip.

10. A method as in claim 9, in which:
    step (d) comprises forming the titanium sublayer to a thickness of approximately 200-1,000 angstroms; and
    step (a) comprises forming the nitride sublayer to a thickness of approximately 500-1,500 angstroms.

* * * * *